US005693512A

United States Patent [19]
Finer et al.

[11] Patent Number: 5,693,512
[45] Date of Patent: Dec. 2, 1997

[54] METHOD FOR TRANSFORMING PLANT TISSUE BY SONICATION

[75] Inventors: John J. Finer; Harold N. Trick, both of Wooster, Ohio

[73] Assignee: The Ohio State Research Foundation, Columbus, Ohio

[21] Appl. No.: 609,794

[22] Filed: Mar. 1, 1996

[51] Int. Cl.$^6$ .................... C12N 13/00; C12N 15/63
[52] U.S. Cl. ........................ 435/173.5; 435/320.1
[58] Field of Search .................... 435/173.5, 320.1

[56] References Cited

U.S. PATENT DOCUMENTS

| | | | |
|---|---|---|---|
| 5,416,011 | 5/1995 | Hinchee et al. | 435/172.3 |
| 5,480,789 | 1/1996 | Firoozabady et al. | 435/172.3 |

FOREIGN PATENT DOCUMENTS

WO 94/02620  2/1994  WIPO.

OTHER PUBLICATIONS

Joersbo et al. Direct gene transfer to plant protoplast by mild sonication. Plant Cell Reports. 9:207–210, 1990.
Zhang et al. Efficient transformation of tobacco by ultrasonication. Bio Technology. 9:996–997, 1991.
Joersbo et al. Sonication: a new method for gene transfer to plants. Physiologia Plantarum. 85:230–234, 1992.
Van Vloten–Doting, et al. Plant–virus–based vectors for gene transfer will be of limited use because of the high error frequency during viral RNA synthesis. Plant Molecular Biology. 4:323–326, 1985.
De Greve et al. Regeneration of normal and fertile plants that express octopine synthase, from tobacco crown galls after deletion of tumour–controlling functions. Nature. 300:752–755, 1982.
"Agrobacterium–mediated Transformation of Walnut Somatic Embryos and Regeneration of Transgenic Plants" by McGranahan, et al. *Biotechnology*, vol. 6, Jul. 1988, pp. 800–804.
"Direct gene transfer to plant protoplasts by mild sonication" by Joersbo, et al., *Plant Cell Reports*, (1990)9: 207–210.

"Sonication: A new method for gene transfer to plants" by Joersbo, et al., *Physiologia Plantarium*, 85: 230–234, Copenhagen, 1992.
"Gene Transfer into Maize by Ultrasonication" by Hong, et al., *Agricultural Biotechnology: Proceedings of Asia–Pacific Conf. on Agricultural Biotechnology*, Aug. 1992, pp. 311–312.
"Efficient Transformation of Tobacco by Ultrasonication" by Zhang, et al., *Biotechnology*, 9: 996–997 (1991).
"Direct Gene Transfer into Wheat Somatic Cells by Ultrasonic Treatment of Immature Embryos" by Xu, et al., *Agricultural Biotechnology: Proceedings of Asia–Pacific Conf. on Agricultural Biotechnology*, Aug. 1992, pp. 294–295.
"Agrobacterium–mediated delivery of infectious maize streak virus into maize plants" by Grimsley, et al., *Nature*, vol. 325, Jan. 1987, pp. 177–179.
"Regeneration of Intact Tobacco Plants Containing Full Length Copies of Genetically Engineered T–DNA and Transmission of T–DNA to R1 Progeny" by Barton, et al., *Cell*, vol. 32, pp. 1033–1043, Apr. 1983.

*Primary Examiner*—Douglas W. Robinson
*Assistant Examiner*—Thanda Wai
*Attorney, Agent, or Firm*—Calfee Halter & Griswold LLP

[57] ABSTRACT

The present invention provides an efficient, cost effective method for transforming, including stably transforming, plants including monocots, dicots and gymnosperms. The method of the present invention, which is less labor intensive than typical conventional transformation methods, comprises combining the plant and a vector which contains the foreign nucleic acid to be introduced into the plant sample. Preferably the plant sample is sonicated in the presence of the vector. The vector is preferably non-tumor inducing bacteria, more preferably Agrobacterium. The sonication duration is less than 15 minutes, preferably less than 6 minutes more preferably 60 seconds or less. After sonicating the plant sample is cultured under conditions that induce morphogenesis to produce plant tissue that will mature into a transformed plant.

19 Claims, 6 Drawing Sheets

5 SEC. SONICATION - DAY 2

COWPEA LEAF
0 SAAT
33X

COWPEA LEAF
10 SAAT
33X

METHOD FOR TRANSFORMING PLANT TISSUE BY SONICATION

BACKGROUND OF THE INVENTION

The introduction of genetic material into plants permits the development of plants that have desirable traits such as disease resistance, improved seed quality, and insect resistance. However, introducing nucleic acid into plants has proven difficult in part due to the presence of the cell wall. Agrobacterium is a bacterial vector that has been used to introduce DNA into certain plant cells. However, Agrobacterium has limitations, including a low rate of transformation. Indeed, many species such as soybeans and maize are not easily transformed by Agrobacterium. In those species where Agrobacterium does transform, incisions often need to be made in the tissue to promote introduction of the Agrobacterium. Unfortunately, such a method is extremely labor intensive and still produces only a limited percentage of transformed plant tissue. Incisions are not even an option for transforming plant cells in suspensions.

Other methods of transformation, such as chemically induced transformations, electroporation, microinjection and particle bombardment each present drawbacks. Chemically induced transformation, such as with by polyethylene glycol, is often toxic to many plants. Moreover, polyethylene glycol is primarily useful for transforming protoplasts; numerous plants including soybeans and maize can't be consistently regenerated from protoplasts. Electroporation, microinjection and particle bombardment are labor intensive, expensive, require sophisticated equipment and produce low levels of transformation. Electroporation is difficult to perform on cells and whole plants. Particle bombardment tends to fragment genes and multiple copies of the same gene linked together tend to be inserted; thus the number of plants that consistently express the desired gene are limited. Polyethylene glycol, electroporation and particle bombardment all insert multiple copies of the gene into the plant, at multiple locations, so that the gene is often not expressed. In addition, it is difficult to control where the DNA inserts, or how many copies. Particle bombardment also has low efficiency particularly where the target tissue lies below the surface.

These and other methods of transformations which a forsake vector and employ naked DNA can also result in degradation of DNA.

It would be desirable to have a method for transforming plants that is not labor intensive, is suitable in gymnosperms, monocots, and dicots, including soybeans, and produces a high yield of transformations.

SUMMARY OF THE INVENTION

The present invention provides an efficient, cost effective method for transforming, including stably transforming, plants including monocots, dicots and gymnosperms. The method of the present invention, which is less labor intensive than typical conventional transformation methods, comprises combining the plant sample and a vector which contains the foreign nucleic acid to be introduced into the plant sample, and sonicating the plant sample. Preferably, the plant sample is sonicated in the presence of the vector. The vector is preferably bacteria, more preferably non-tumor inducing Agrobacterium. The sonication duration is preferably less than 15 minutes, more preferably less than 6 minutes, most preferably 60 seconds or less. After sonication, the plant sample is cultured under conditions that induce morphogenesis to produce plant tissue that will mature into a transformed plant.

DETAILED DESCRIPTION OF THE INVENTION

Figure 1:
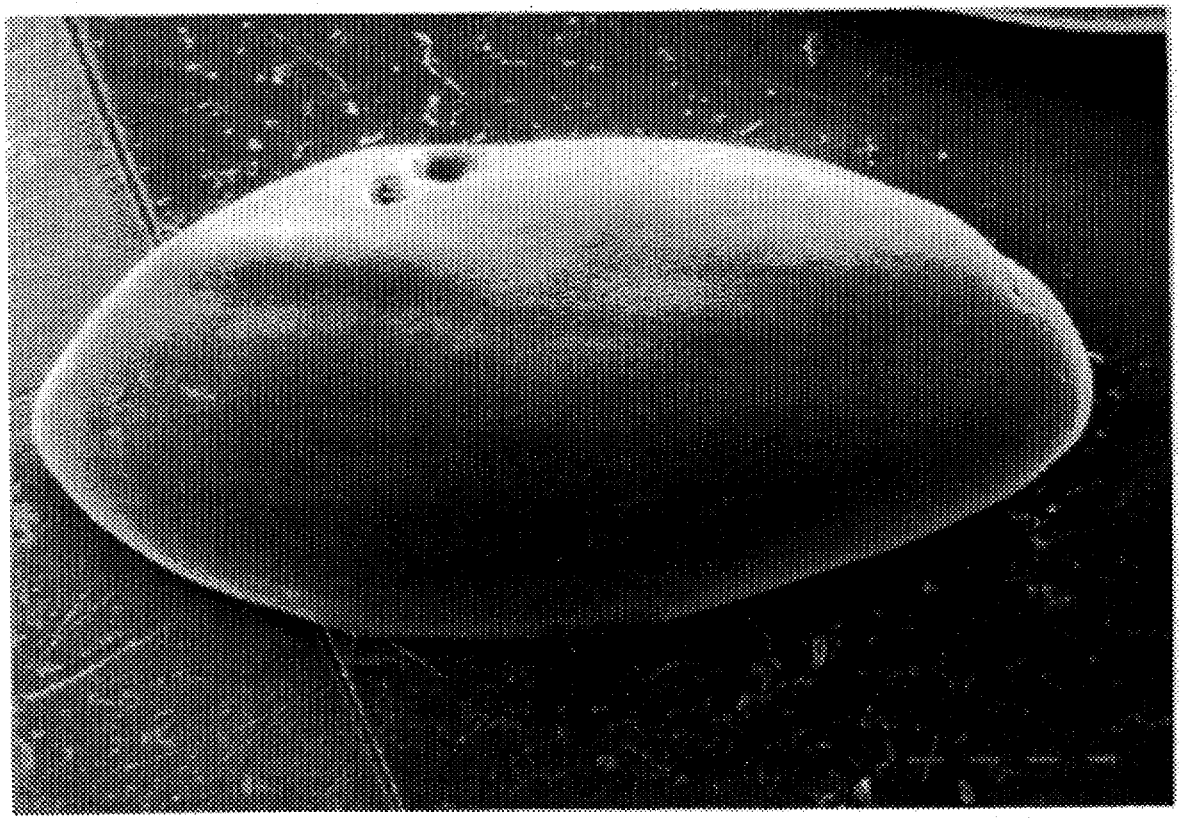
FIG. 1 is a scanning electron micrograph of a non-sonicated control soybean cotyledon at a magnification of 40× at day 0.

The method of the present invention, which increases the rate of transformation in plants, comprises exposing the plant sample to a vector containing the foreign nucleic acid and sonicating the plant sample. Preferably, the plant sample is sonicated in the presence of the vector which is preferably non-tumor inducing Agrobacterium. The method of the present invention is not limited to a particular form of plant cell or plant tissue; suitable plant material to be transformed includes whole plants as well as all the parts and portions thereof, including but not limited to, plant tissues, cells, aggregates of cells, seeds, immature cotyledons, cotyledonary nodes, embryos, leaves, roots, meristems, pollen, shoot tips, flowers, flower stalks, seedlings, plant cell tissue culture or plant tissue culture. Thus as used herein "sample" includes whole plants as well as all the parts and portions thereof, including but not limited to, plant tissues, cells, aggregates of cells, seeds, immature cotyledons, cotyledonary nodes, embryos, leaves, roots, meristems, pollen, shoot tips, flowers, flower stalks, seedlings, plant cell tissue culture or plant tissue culture.

The method of transformation is useful in dicots, monocots and gymnosperms. A wide variety of plant species are transformed according to the method of the present invention; representative examples include such diverse species as soybean, buckeye, tobacco, cowpea, corn, wheat, and spruce.

The method of the present invention has the further advantage in that it is useful for producing stable transformants. Also the method is preferably conducted at 4°–37° C., more preferably about 23°–30° C.

The Vector

The vector employed in producing transformants contains the foreign nucleic acid. The vector is a non-tumor inducing bacteria or strain of bacteria, preferably of the family Rhizoblaceae more preferably Agrobacterium, more preferably *Agrobacterium tumefaciens* or *Agrobacterium rhizogenes*.

The Foreign Nucleic Acid

The foreign nucleic acid which includes DNA and RNA, is the nucleic acid to be inserted into the plant to produce the transformant. Preferably the foreign nucleic acid is one or more genes which is preferably contained in a plasmid. Such plasmid is located within the vector. Plasmids containing foreign nucleic acid, are available commercially, or may be created using conventional methods. The plasmid is then introduced into the vector using conventional methods. The specific nucleic acid is selected according to the desired properties of the transformant. Where the vector is Agrobacterium, it is preferred that the foreign nucleic acid be inserted into a binary plasmid which is the inserted into the Agrobacterium. The Agrobacterium binds to the plant cell walls and transfers defined DNA regions to the plant cell.

Good results have been obtained using the β-glucuronidase gene, hereinafter also referred to as the "GUS" gene with a hygromycin antibiotic resistance gene. For example, the plasmid pIG121Hm contains the GUS coding region under the regulatory control of the CaMV35S promoter with a castor bean intron which does not allow expression of GUS in the bacteria. Plasmid pIG121Hm also contains a hygromycin resistance gene driven by a CaMV35S promoter and a kanamycin resistance gene driven by a nopaline synthase promoter. This plasmid is described in Hiei, et al., "Efficient transformation of rice (Oryza satira L.) mediated by Agrobacterium and sequence analysis of the boundaries of the T-DNA", *The Plant Journal* (1994), 6(2):271–282.

The Vec035 plasmid contains the GUS coding region under the regulatory control of the CaMV35S promoter with a potato intron. The Vec035 plasmid also contains a hygromycin resistance gene driven by a nopaline synthase promoter. The plasmid Vec035 is constructed by replacing the GUS gene in the plasmid pBIG-HYG, as described in Becker, D., "Binary vectors which allow the exchange of plant selectable markers and reporter genes", *Nucleic Acids Research* (1990) Vol. 18, No. 1, 1990, pp. 203, with the intron-containing GUS gene from p35SGUSINT as described in Vancanneyt, et al., "Construction of an intron-containing marker gene: Splicing of the intron in transgenic plant transformation", *Molecular General Genetics* (1990), 220:245–250.

The plasmid p35SGUSINT contains the GUS coding region under the regulatory control of the CaMV35S promoter with a potato intron. The plasmid p35SGUSINT also contains a kanamycin resistance gene driven by the hopaline synthase promoter. This plasmid is described in Vancanneyt, et al., *Molecular General Genetics* (1990), 220:245–250.

The presence of an intron in the GUS gene renders the GUS non-functional in bacteria; the bacteria cannot process the intron to restore function. When the GUS gene is introduced in to the plant sample, the plant cells splice out the intron to provide a functional gene which produces β-glucuronidase. β-glucuronidase, which is not normally made by plants is thus used to identify transformant plant sample. In the presence of an assay solution which contains chromogenic substrate, the transformant produces blue pigment which is easily detected by visual observation.

Plasmids are introduced into the bacterial vector using conventional methods. For example, plasmid pIG121Hm was introduced in strain EHA 105 by electroporation employing ElectroCell manipulator ECM600, from BTX Inc. San Diego, Calif., according to the manufacturer's instructions contained in protocol number PR004 in the ElectroCell manipulator ECM600 Electroporation System Operation Manual. Triparental mating procedure is also suitable; see for example Golds, T. J. et. al. (1990) "Methods of Gene transfer and analysis in Higher Plants" in Methods in Molecular Biology, Vol. 6 Plant Cell and Tissue Culture J. W. Pollard and J. M. Walker, editors pp 341–371. Electroporation and Triparental mating procedures are also suitable for introducing plasmid 35SGUSINT into *Agrobacterium tumefaciens* strains GV3850 and GV2260 according to the methods stated in the above listed references.

Plant Sample Preparation

Plant samples are preferably prepared by surface sterilization using conventional sterilization methods, then aseptically excising the portion of the plant that is to be transformed. Good results have been obtained using a solution containing 20% Clorox® bleach, 0.02% Tween-20 to surface sterilize the plant sample followed by slight agitation for 20 minutes and rinsing three times with sterile distilled water. Intact non-sterile plants or plant tissues are also suitable.

Preparation of the Vector

The vector is preferably prepared in suspension on growth medium or a semi-solid medium. Good results have been obtained for Agrobacterium by growing overnight in 10 ml LBS media with 100 μg/μl kanamycin at 28° C. while shaking at 150 rpm. Log phase Agrobacterium cells are then centrifuged at 1500×g for 10 minutes, resuspended in 10 ml of the same liquid plant culture medium to be used to culture transformants, re-centrifuged and resuspended in 10 ml of the same medium. Preferably the vector is suspended in the same culture media that will be used to culture the transformants. The $OD_{600\ nm}$ is then determined against a medium blank. Preferably the bacteria is diluted to an $OD_{600\ nm}$ between 0.01 and 0.5 with medium.

Transformation of Plant Sample

Sonication of the Plant Sample

Preferably from about 0.5 to about 1.0 ml of Agrobacterium suspension diluted to an optical density of $OD_{600\ nm}$ of from about 0.1 to about 0.5 is combined with the plant sample to be transformed. The vector is combined with the plant sample before, during or after sonication; however, sonicating the plant sample in the presence of the vector is preferred.

The plant sample is sonicated for a duration sufficient to transform the plant cell/tissue, preferably from 0.01 seconds to about 15 minutes, more preferably about 0.2 seconds to about 5 minutes, most preferably about 1 second to about 1 minute. Sonication periods longer than 15 minutes are less preferred because such times typically decrease the viability of the plant sample. The optimum sonication duration depends upon the sample being sonicated, and the sonicator being used. When sonicating with a probe sonicator typically less time is needed than with a bath sonicator.

While a variety of vessels are suitable for holding the plant sample during sonication, when using the bath sonicator, the 13×100 mm borosilicate tubes are preferred for immature cotyledons, 13×100mm borosilicate tubes are preferred for soybean embryos. 23×150 mm borosilicate tubes are preferred for tobacco leaves and seedlings. For soybean meristem and tobacco leaves and seedlings, 50 ml borosilicate tubes or 50 ml polypropylene tubes are suitable.

For immature cotyledons the preferred sonication duration with a bath sonicator is from about 1 to 300 seconds, more preferably about 2 to 15 seconds. For leaf tissue the preferred sonication duration with a bath sonicator is from about 0.2 seconds to 300 seconds, most preferably about 10 to 60 seconds. For shoot tips, apices and meristems the preferred sonication duration with a probe sonicator is from about 5 seconds to 300 seconds, more preferably about 30 to 120 seconds, most preferably about 60 seconds. For embryonic suspensions the preferred sonication duration with a bath sonicator is from about 2 seconds to 300 seconds, more preferably 5 seconds to 120 seconds, most preferably about 10 to 60 seconds. For seedlings, the preferred sonication duration is about 0.2 to 600 seconds, more preferably about 5 to 300 seconds, most preferably about 10 to 100 seconds.

Figure 2:
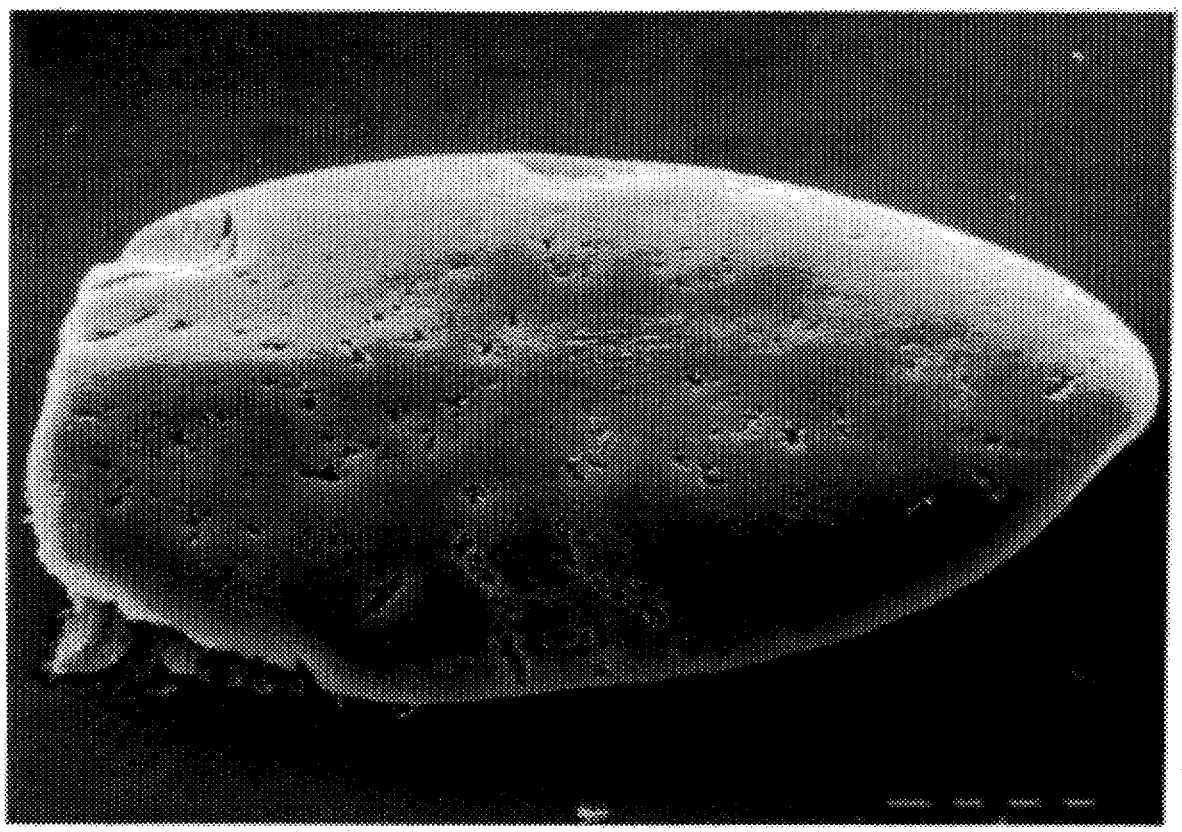
FIG. 2 is an electron micrograph, 50× magnification showing a soybean cotyledon treated according to Example 1, at day 0 shortly after a 5 second sonication in the presence of Agrobacterium.
Figure 3:
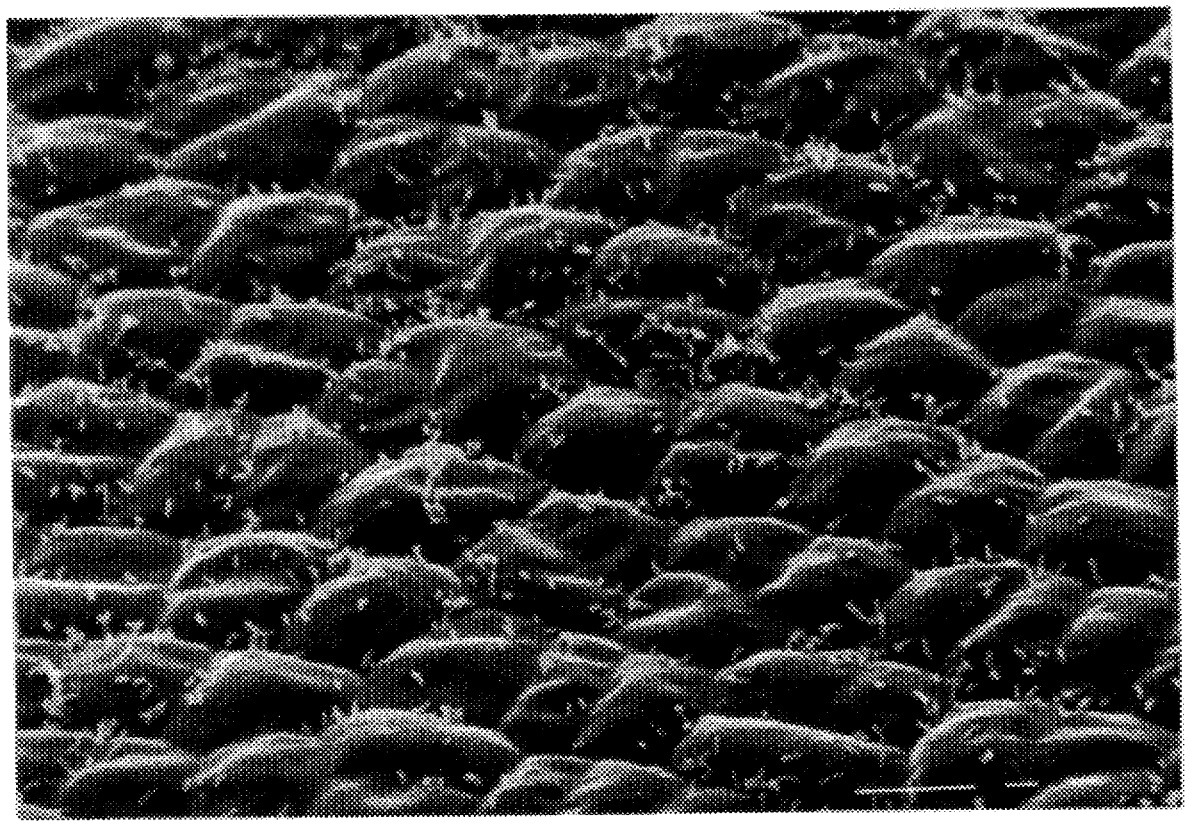
FIG. 3 is an electron micrograph of a control soybean cotyledon that was not sonicated, treated according to Example 1, at a magnification of 1,500× at day 2.
Figure 4:
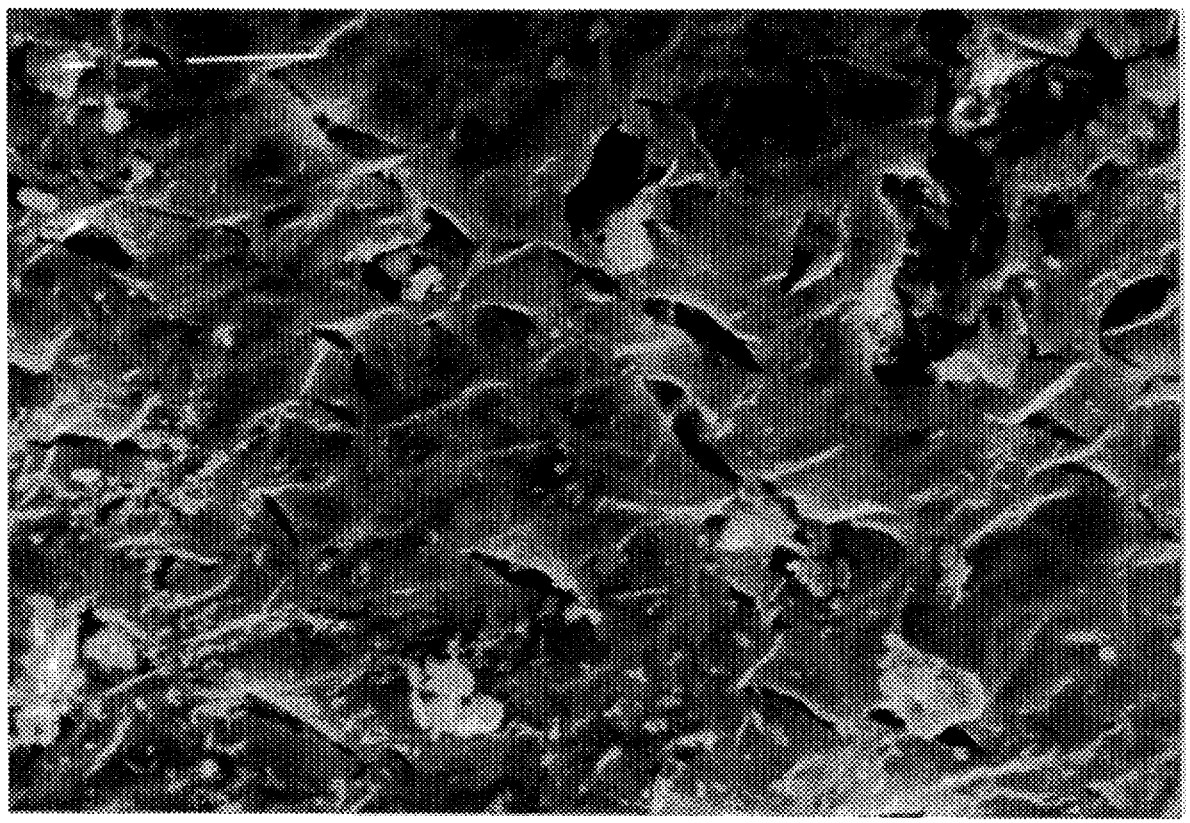
FIG. 4 is an electron micrograph, 1,300× magnification showing a soybean cotyledon treated according to Example 1, at day two after 5 second sonication in the presence of Agrobacterium.
Figure 5:
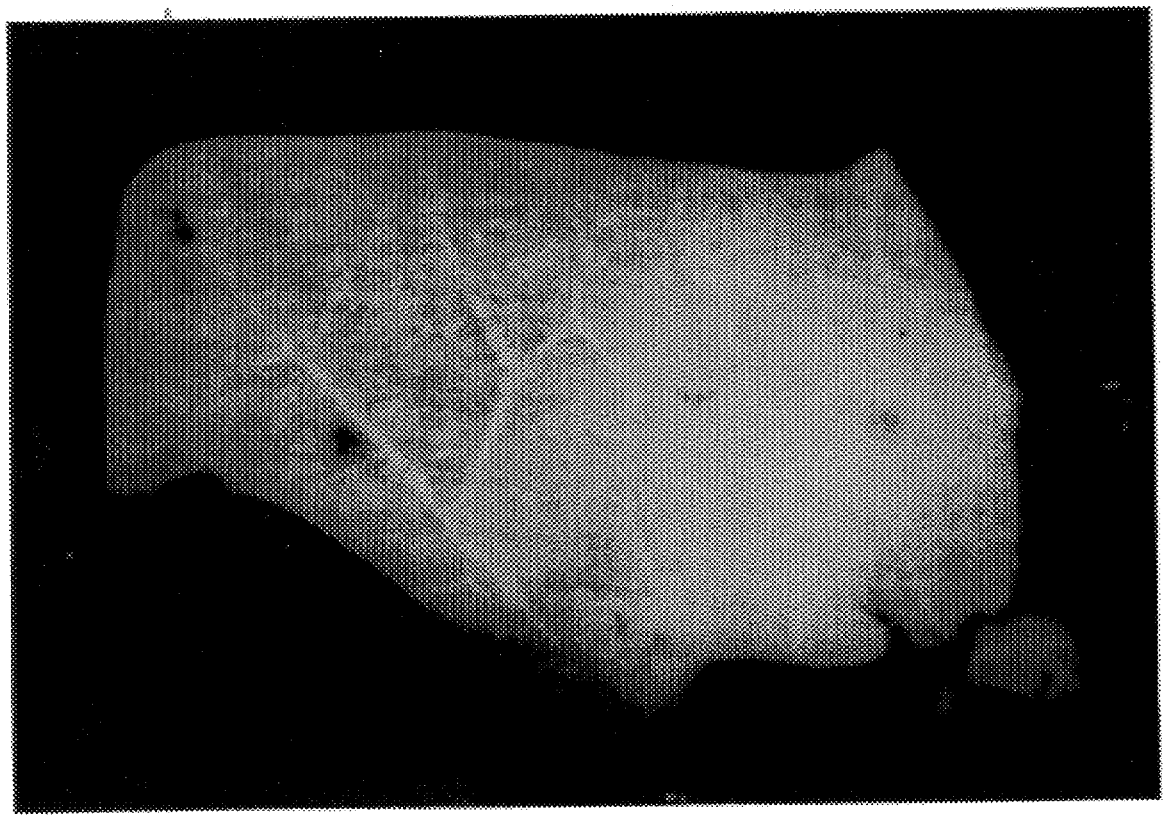
FIG. 5 is a photograph at 33× magnification showing a control non-sonicated cowpea leaf according to Example 16; the dark spots are areas of transformation at day 4.
Figure 6:
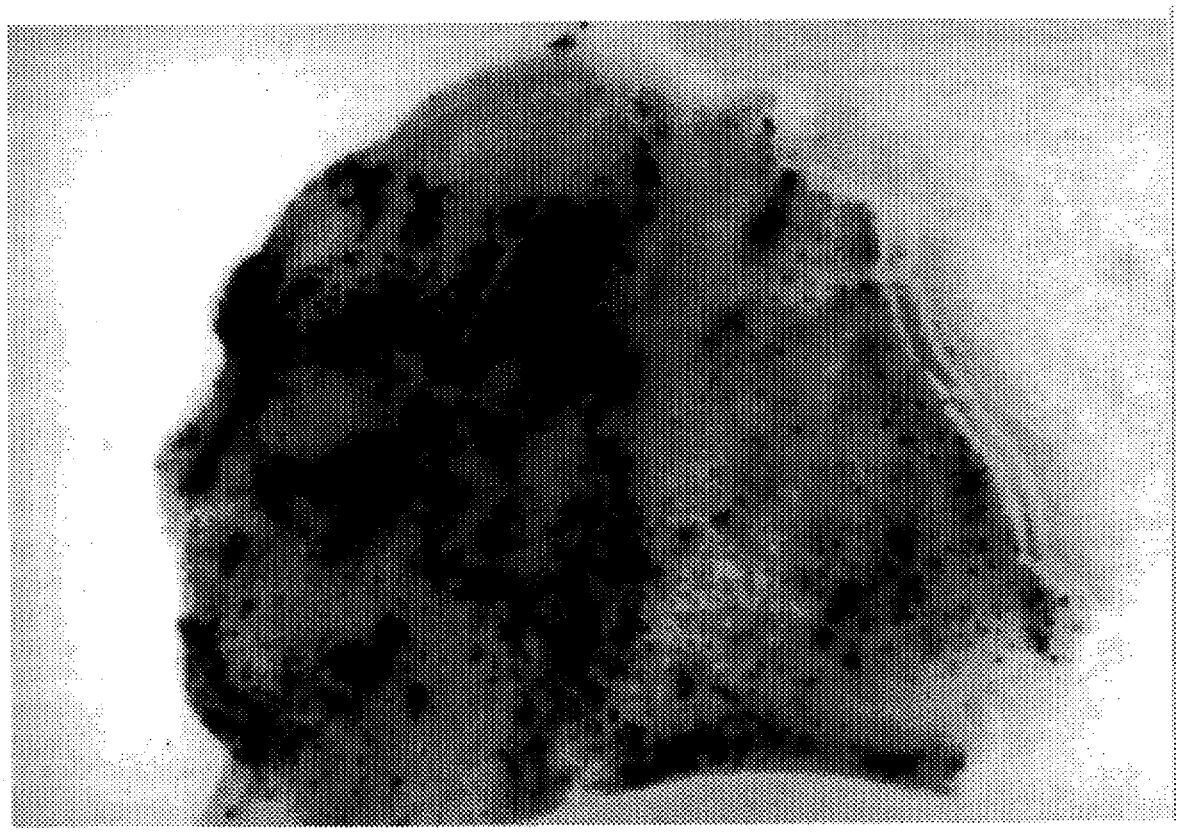
FIG. 6 is a photograph, 33× magnification showing a section of a cowpea leaf receiving a 10 second sonication according to Example 16; the dark spots are areas transformed with the glucuronidase gene at day 4.

Conventional sonicators are suitable. Good results have been obtained using: bath sonicator model FS5, available from Fisher Scientific, Fisherbrand, bath sonicator from L & R Manufacturing, Kearny, N.J., and a probe sonicator from Branson Ultrasonics Corporation, Sonifier Model #350. A range of sonication frequencies are suitable for sonication of the plant sample, good results have been obtained using a frequency of 55 KHZ in the bath sonicator and 20 KHZ with a probe sonicator. A range of powers are suitable for sonication of the plant sample; the higher the wattage employed, the lower the sonication duration. Good results have been obtained using 10 to 300 watts, preferably 106 watts in a bath sonicator, and 5 to 100 watts with a probe sonicator. Where the plant tissue is primarily green after sonication the tissue is not damaged by the sonication. However, the presence of white tissue immediately after sonication indicates dead tissue and either the power or duration should be decreased. Where bath sonicators are used, the best results are typically obtained when tube is suspended in center of sonicator bath. An examination of sonicated plant samples at day 0 reveals minute fissures. As shown in the FIG. 1, the control cotyledons, that is, non-sonicated cotyledons have a smooth surface; the holes present on the surface are caused by the forceps during specimen preparation. In comparison as shown in FIG. 2, the sonication produced holes in the cotyledons. Agrobacterium are seen still on the surface of the cotyledons, as shown in FIGS. 3 and 4 at day 2. FIG. 5 shows a non-sonicated piece of leaf. FIG. 6 shows a sonicated leaf showing the transformed areas. The fissures that result from the sonication typically average 1.2 to 30 microns; although larger figures 100 to 500 microns are occasionally observed. Fissures are typically formed deep within the plant tissue; the vector can penetrate 10 to 15 or more cell layers.

Post Sonication Growth of Plant Sample

After sonication, the plant sample is removed, preferably for 30 seconds to one hour and preferably blotted with filter paper to remove excess bacteria. Washing the plant sample after sonication is also suitable for removing excess bacteria.

The plant sample is then placed on a culture medium, referred to herein as an "induction media," to induce growth, either to continue proliferation or to induce embryogenesis, shoot morphogenesis, shoot elongation, germination or morphogenesis of the plant sample. Preferably the media lacks an agent which inhibits the vector growth. Preferably, the plant signal molecule acetosyringone is present in the medium. Preferably, the acetosyringone is present in the culture medium at a concentration of from about 1 µM to about 1 mM, more preferably from about 100 µm to about 200 µm. In some strains of Agrobacterium acetosyringone induces the Vir genes of Agrobacterium and enhances transformation rates. The acetosyringone is not necessary since the sonication method transforms plants, including soybeans, even in the absence of the acetosyringone. Good results have been obtained using about 100 µM acetosyringone. While the plant sample may be left on the induction media a week or more, it is preferred that the plant remain on the induction media for about 2 to 3 days.

Next, the sample is removed from the induction media, preferably rinsed with distilled water or liquid media and transferred to the induction medium with antibiotics to promote growth of induced tissues. Preferably an antibiotic is present in the medium to control, or more preferably, to inhibit, bacterial vector growth. Where the vector is Agrobacterium, good results have been obtained using 400 µg/ml of the antibiotic Timentin®, a mixture of ticarcillin and clavulanic acid, in a ratio of 20 to 1, or 500 µg/ml of the antibiotic cefotaxime. While the plant sample may be left in such antibiotic containing medium for 60 days, good results have been obtained by culturing for about 10 days. Thereafter, a portion of the plant sample is typically assayed for the presence of the foreign nucleic acid or the protein that such nucleic acid encodes.

Selection for Transformants

Next, the plant sample is removed from the induction medium with antibiotics and transferred to a selection medium. The transformants are grown typically for about 5 to about 120 days, preferably about 30 days on a the selection medium. The selection medium is a growth medium that contains a selective agent such as an antibiotic or herbicide that will selectively kill plant tissue; that is, plant cells that did not receive the resistance gene from the foreign DNA carried by the vector will be killed. Where the plant resistance gene is hygromycin resistance, good results have been obtained using 20 mg/L hygromycin to select for the transformant. Where the plant resistance gene is kanamycin resistance, good results have been obtained using 100 mg/L kanamycin to select for the transformant.

Preferably, the selection media also contains an inhibitory agent such as an antibiotic to control or inhibit the vector growth. Good results were obtained using 400 to 500 mg/L of the antibiotic cefotaxime to control the vector Agrobacterium growth. The sample is typically transferred to fresh media about every one to three weeks. Thereafter, a portion of the plant sample are typically assayed for the presence of the foreign nucleic acid or the protein that such nucleic acid encodes.

Where the transformation is transient, that is the foreign DNA remains in the cytoplasm of the target plant cell, then the DNA is degraded typically in two to seven days although the protein product of such foreign DNA may remain in the cell for a longer period of time. Thus to distinguish the transiently transformed cells from the stably transformed cells, it is preferred that the cells be cultured for at least 45 days. Cells expressing the foreign nucleic acid at 45 days or more indicates that the transformation is stable, that is the foreign DNA was inserted into the genetic material of the target plant cell. Stable transformation is confirmed by conventional analysis such as Southern hybridization analysis or polymerase chain reaction techniques; however such confirmation consumes the transformant. Moreover, a portion of the cells/tissue collected after the selection process are preferably specifically assayed for the activity of the foreign gene.

Assay for Inserted Gene Activity

Where the foreign gene is the GUS gene, the presence of the gene is determined by the following assay. It will be appreciated however, that where the DNA to be inserted does not include the GUS gene another suitable assay is employed. The β-glucuronidase gene expression was assayed by placing transformed plant sample in β-glucuronidase assay solution which contained: 10 mM $Na_2EDTA$ in water, 0.1% Triton X-100, 0.1M $NaH_2PO_4$, 0.5M $K_3Fe(CN)_6$ and 250 µg/ml 5-bromo-4-chloro-3-indolyl β-glucuronide. The plant sample samples were incubated overnight with gentle agitation at 37° C. The plant sample containing and expressing the β-glucuronidase gene are able to cleave the glucuronic acid from a chromogen. The product of the assay appears as a blue pigment on the transformed plant sample. The plant sample was then visually examined and the quantity of blue spots or the percent of the surface areas that were blue, were determined.

Media Compositions

The following media were used in the Examples described herein.

The D-40 media contains: MS salts as disclosed in Murashige and Skoog, (1962) Physiological Plant 15:473–498; B5 vitamins, as disclosed in Gamborg et al. (1968) Experimental Cell Research 50:151–158; 6% sucrose; 40 mg/L 2,4-dichlorophenoxyacetic acid, available from Sigma Chemical Company, St. Louis, Mo.; and either 0.2% Gelrite available from Kelco, Chicago, Ill. or 0.8% agar at a pH of about 7.0, unless the pH is noted otherwise. Where the D-40 media is identified as "liquid" such media lacks both the Gelrite and agar.

The ½ OMS media contains ½ MS salts and ½ B5 vitamins as in the D-40 media; 1.5% sucrose; 0.2% Gelrite at a pH of about 5.7.

The Finer-Nagasawa medium also referred to herein as the "FN" medium contains: the MS salts modified to contain 10 mM $NH_4NO_3$ and 30 mM $KNO_3$ and the B5 vitamins as in the D-40 media; 6% sucrose 5 mg/L 2,4-dichlorophenoxyacetic acid; and 5 mM asparagine at pH of about 5.7.

The LBS media contains 10 g/L tryptone, 5 g/L yeast extract; 5 g/L NaCl, and 5 g/L sucrose at pH 7.

The CM media contains: MS salts and B5 vitamins as in the D-40 media; 3% sucrose; 1 mg/L benzyladenine, 0.1 mg/L naphthalene acetic acid and 0.2% Gelrite at a pH of about 5.7.

The 2T2S media contains: MS salts and B5 vitamins as in the D-40 medium; 2% sucrose; and 2 mg/L 2,4-dichlorophenoxyacetic acid.

EXAMPLES

The procedures in the following examples were conducted at 26° C. to 28° C. unless otherwise noted. In the following examples, greater than 90% of the plant tissue was green immediately after sonication indicating a viability of greater than 90%.

The following *Agrobacterium tumefaciens* strains were employed in the examples: EHA 105 which is described in Hood et. al., "New Agrobacterium helper plasmids for gene transfer to plants", Transgenic Research, 2, 208–218 (1993) which contained either the binary plasmid Vec035 or pIG121Hm; GV3850 which contains Ti plasmid pGV3850 the construction of which is described in Zambryski, et. al, "Ti plasmid vector for the introduction of DNA into plant cells without alteration of their normal regeneration capacity", *The EMBO Journal*, Vol. 2, No. 12, pp. 2143–2150, 1983, and the binary plasmid p35SGUSINT; and GV2260 which contains Ti plasmid pGV2260 the construction of which is described in Deblaere, et. al., "Efficient octopine Ti plasmid-derived vectors for Agrobacterium-mediated gene transfer to plants", Nucleic Acids Research, Vol. 13, No. 13, pp. 4777–4788, 1985, and the binary plasmid p35SGUSINT.

The following examples are illustrative and not intended to limit the scope of the invention.

Example 1

Soybean Cotyledons

Immature soybean pods of the variety Chapman were collected, surface sterilized in 20% Clorox® bleach, 0.02% Tween-20, with slight agitation for 20 minutes and then rinsed three times with sterile distilled water. Immature cotyledons, 3–5 mm length, were aseptically excised by cutting the embryo axis off of the cotyledons and then pushing the cotyledons out of the seed coat. The cotyledons were placed on D40 medium at pH 7.0 until enough were collected for treatment.

Log phase Agrobacterium EHA 105 cells containing Vec035 were centrifuged at 1500×g for 10 minutes, resuspended in liquid D40 medium, re-centrifuged at 1500×g for 10 minutes, and resuspended in liquid D40. The $OD_{600\ nm}$ was then determined against a liquid D40 medium blank. The bacteria were then diluted to an $OD_{600\ nm}$ of 0.5 with liquid D40 medium.

The cotyledons were transferred to 1.5 ml microcentrifuge tubes, from Eppendorf containing 0.5 ml of the diluted Agrobacterium suspension. The cotyledons were suspended in this volume by mild agitation and placed in a float at the center of a bath sonicator from Fisher Scientific, Model FS5 which was controlled with an electronic timer. The cotyledons were sonicated for either 0.2 seconds, 1 second, 2 seconds, 5 seconds or 10 seconds at 55 KHZ, generating either horizontal or vertical waves or both. A control group of cotyledons was not sonicated. The bath sonicator contained between 500 and 750 ml of a 1:20 dilution of an ultrasonic cleaning solution, available from Fisher, catalog number 15-336-26.

After the sonication, the cotyledons were removed from the microcentrifuge tube, placed on a sterile filter paper to blot off excess bacteria, and then transferred to D40 medium containing 100 μM acetosyringone, flat side, that is, adaxial side, up. After two days of co-culture, the cotyledons were washed in sterile distilled water, blot-dried on sterile filter paper, and placed flat side up onto D40 medium which contained 350 mg/L cefotaxime. Four days after sonication, the β-glucuronidase expression was assayed and the percent of surface area exhibiting blue sections, was measured. The results are presented below in Table I.

TABLE I

Transformation of Sonicated Soybean "Chapman" Cotyledons

| Sonication Duration (sec) | Number of Cotyledons | Percent Surface Area Transformed (±SD) |
|---|---|---|
| 0 | 33 | 0.2 ± 0.4 |
| 0.2 | 37 | 24.2 ± 22.6 |
| 1 | 29 | 42.8 ± 26.1 |
| 2 | 48 | 38.4 ± 28.2 |
| 5 | 34 | 53.6 ± 25.1 |
| 10 | 10 | 75.1 ± 15.6 |

The results, which are the accumulation of five independent experiments, show that even after 0.2 seconds of sonication, that 24.2% of the cotyledon surface expressed the β-glucuronidase gene in contrast to 0.2% in the controls. The percent of expression increases as the duration of the sonication increases. At a duration of 1 and 2 seconds the percent increases transformation to 42.8 and 38.4 respectively. Increasing the sonication to about 5 seconds leads to an increased transformation of about 53.6, while a 10 second sonication leads to expression of the β-glucuronidase gene over 75% of the surface area.

Example 1A

Immature Chapman cotyledons were treated as in Example 1, except that the cotyledons were sonicated in the absence of Agrobacterium. These cotyledons were first sonicated in 0.5 ml in liquid D40 media for the durations presented in Table 1A, then within about five minutes the D40 media was replaced with the 0.1 O.D.$_{600\ nm}$ Agrobacterium suspension. The cotyledons remained in the suspension for five minutes then were blot dried on filter paper and transferred to solid D40 medium. The results are presented in Table 1A.

TABLE 1A

PERCENT OF SURFACE AREA OF IMMATURE SOYBEAN COTYLEDONS TRANSFORMED

| | Percent of surface area transformed | |
|---|---|---|
| Sonication duration (sec) | Sonication with Agrobacterium | Sonication before addition of Agrobacterium |
| 0 | 0.8 ± 1.8 | 0.6 ± 1.8 |
| 1 | 48 ± 23 | 39 ± 25 |
| 2 | 67 ± 35 | 56 ± 28 |
| 5 | 62 ± 23 | 68 ± 10 |
| 10 | 79 ± 9 | 54 ± 35 |

As shown in Table 1A, sonicating in the presence of Agrobacterium and sonicating before the Agrobacterium are both effective methods of transforming tissue.

Example 1B

Immature cotyledons from the soybean cultivar "Jack" were treated as described in Example 1 except that the cotyledons were sonicated for 1 second and co-cultured with either Agrobacterium EHA 105 containing pIG121Hm or Agrobacterium EHA 105 containing Vec035. The Agrobacterium had an O.D.$_{600\ nm}$ of 0.1. These Agrobacterium treated cotyledons were then treated as in Example 1.

Additional cotyledons were sonicated in the absence of Agrobacterium as in Example 1A except they were sonicated for either 1 or 2 seconds, then placed on solid D40 medium containing 100 μM acetosyringone for one day. Thereafter, the cotyledons were immersed in 1.0 ml of Agrobacterium, and co-cultured with either Agrobacterium EHA105 containing pIG121Hm or Agrobacterium EHA105 containing Vec035 for 60 minutes. The Agrobacterium had an O.D.$_{600\ nm}$ 0.1. The cotyledons were then blotted on filter paper and placed on solid D40 medium containing 100 μM acetosyringone for two days. The cotyledons were then transferred to D40 medium containing 500 mg/L cefotaxmine for two days and then assayed for GUS expression. The results are presented in Table 1B.

TABLE 1B

Effect of co-culture of immature soybean cotyledons with Agrobacterium either during or the day following sonication

| | Percent of surface area transformed | |
|---|---|---|
| Treatment | EHA 105 (Vec035) | EHA 105 (pIG121Hm) |
| 0 sonication (control) | 0.0 | 0.0 |
| 1 sec. sonication with Agrobacterium | 21 ± 14.3 | 5.3 ± 4.0 |
| 0 sec. sonication Agrobacterium added 1 day* (control) | 0.0 | 0.0 |
| 1 sec. sonication, | 9.6 ± 9.5 | 20 ± 7.6 |

TABLE 1B-continued

Effect of co-culture of immature soybean cotyledons with Agrobacterium either during or the day following sonication

| | Percent of surface area transformed | |
|---|---|---|
| Treatment | EHA 105 (Vec035) | EHA 105 (pIG121Hm) |
| Agrobacterium added one day later | | |
| 2 sec. sonication, Agrobacterium added one day later | 19.2 ± 19.2 | 27.5 ± 28.4 |

*added one day after excising cotyledon

As shown in Table 1B, when compared to the non-sonicated controls, transformation is enhanced where Agrobacterium is added 1 day after sonication.

Example 2

Immature cotyledons from the soybean cultivar "Jack" were treated as described in Example 1, except that the cotyledons were sonicated for 0.2, 1, 2 or 5 seconds. The results are presented below in Table II.

TABLE II

PERCENT TRANSFORMATION IN SONICATED SOYBEAN COTYLEDONS AT VARIOUS SONICATION DURATIONS

| Sonication Duration (sec) | Number of Cotyledons | Percent Surface Area Transformed (±SD) |
|---|---|---|
| 0 | 6 | 0 |
| 0.2 | 10 | 7.4 ± 13 |
| 1 | 10 | 26 ± 18 |
| 2 | 10 | 39 ± 18 |
| 5 | 9 | 45 ± 26 |

As with the Chapman soybeans, sonication also increased the percent transformation of the soybean Jack cotyledons. The transformation efficiency tended to increase as the duration of the sonication increased.

Example 2A

Immature cotyledons from the soybean variety Jack were treated as in Example 1, except that they were sonicated for 5, 15, 30, 60, 120, 300 and 600 seconds. The results are presented below in Table IIA.

TABLE IIA

EFFECT OF VARYING SONICATION DURATION ON TRANSFORMATION

| Sonication Duration (seconds) | Percent Surface Area Transformed (±SD) |
|---|---|
| 0 | 0 |
| 5 | 19.7 ± 18.8 |
| 15 | 6.6 ± 6.0 |
| 30 | 24.1 ± 4.0 |
| 60 | 16.4 ± 14.4 |
| 120 | 11.6 ± 12.3 |
| 300 | 41.6 ± 15.9 |
| 600 | 0 |

Sonication treatments of duration up to and including 15 seconds resulted in green cotyledons. However, sonication treatments 30 seconds and longer damaged the cotyledons and 50% were dead, that is appeared white, after 5 days, and such treatments are less preferred. Soybean cotyledons initially survive the sonication treatment with good levels of gene expression.

Example 3

Soybean Jack cotyledons were treated as in Example 1 except that the sonication lasted for 2 seconds, and the concentration of Agrobacterium EHA 105 containing Vec035, varied from 0.3, 0.1 and 0.05 at $OD_{600}$ nm. The results are presented below in Table III.

TABLE III

PERCENT TRANSFORMATION OF SOYBEAN COTYLEDONS SONICATED WITH VARYING CONCENTRATIONS OF AGROBACTERIUM

| Agrobacterium O.D. (600 nm) | Number of Cotyledons | Percent Surface Area Transformed (±SD) |
|---|---|---|
| 0.3 | 12 | 42 ± 4.2 |
| 0.1 | 12 | 50.7 ± 20.8 |
| 0.05 | 12 | 22.7 ± 27.8 |
| 0.3 non-sonicated control* | 12 | 0.62 ± 1.06 |

*Control - non-sonicated cotyledons that received 0.3 $OD_{600\ nm}$ Agrobacterium The threefold difference in concentration of the Agrobacterium between 0.1 and 0.3 did not lead to a significant difference in the percent of the surface area expressing the β-glucuronidase gene.

Example 4

Immature cotyledons of the soybean cultivar "Chapman" were removed and treated as in Example 1, except that Agrobacterium tumefacients strain GV3850 or GV2260 each containing plasmid p35SGUSINT at $OD_{600}$ nm 0.05 were added, and the cotyledons were sonicated for either 0, 2, or 5 seconds in a Fisher Model FS-5 bath sonicator. The results are presented below in Table IV.

TABLE IV

PERCENT TRANSFORMATION OF SOYBEAN COTYLEDONS SONICATED WITH AGROBACTERIUM TUMEFACIENTS STRAIN GV3850 OR STRAIN GV2260.

| Agrobacterium Strain | Sonication Duration (sec) | Number of Cotyledons | Percent Surface Area Transformed (±SD) |
|---|---|---|---|
| GV3850 | 0 | 6 | 0 |
| GV3850 | 2 | 8 | 33 ± 23 |
| GV3850 | 5 | 8 | 19.9 ± 14.7 |
| GV2260 | 0 | 6 | 0 |
| GV2260 | 2 | 8 | 46 ± 30 |
| GV2260 | 5 | 8 | 49.6 ± 21.6 |

The sonication significantly increased the percent of the cotyledon surface area that was transformed, as compared to the controls. However, of the two strains, the Agrobacterium tumefacients strain GV2260 is preferred.

Example 5

Immature cotyledons from the soybean cultivar "Chapman" were treated as in Example 1, except that the cotyledons were sonicated for 2 seconds and placed on a D-40 medium containing 100 µM acetosyringone for about two days, either adaxial side up or abaxial side up. The cotyledons were then transferred to D-40 medium containing 500 µg/ml of the antibiotic cefotaxime for 2 days, either adaxial side up or down. The results are presented below in Table V.

TABLE V

PERCENT TRANSFORMATION ON ADAXIAL AND ABAXIAL SURFACES OF SOYBEAN COTYLEDONS CO-CULTURED ADAXIAL SIDE UP AND ABAXIAL SIDE UP

| Cultured Adaxial Side Up Percent Surface Area Transformed (±SD) | | Cultured with Abaxial Side Up Percent Surface Area Transformed (± SD) | |
|---|---|---|---|
| adaxial side | abaxial side | adaxial side | abaxial side |
| 19.5 ± 22.5 | 6.1 ± 15.6 | 1.7 ± 3.8 | 30.8 ± 27.7 |

The percent transformation appears to be related to the orientation of the cotyledon. Whichever surface was co-cultured face up had the higher levels of transformation.

Example 6

Immature soybean "Jack" cotyledons were treated as in Example 1 except that they were sonicated for 2 seconds and co-cultured with Agrobacterium $OD_{600\ nm}$ 0.05 and 0.01 for 2, 3 or 4 days. After such co-culture, they were cultured on D40 medium containing either 350 mg/l of the antibiotic cefotaxime or 400 mg/l of the antibiotic Timentin®. Cotyledons were assayed for β-glucuronidase expression two days after the co-culture period. The results are presented below in Table VI.

TABLE VI

COMPARISON OF VARIOUS CO-CULTURE PERIODS ON PERCENT TRANSFORMATION OF SOYBEAN COTYLEDONS

| | Cefotaxime | | Timentin ® antibiotic |
|---|---|---|---|
| Co-culture period | 0.05 $OD_{600nm}$ | 0.01 $OD_{600nm}$ | 0.05 $OD_{600nm}$ |
| Day 2 | 14.7 ± 8.3 | 8.9 ± 5.8 | 8.3 ± 8.6 |
| Day 3 | 31.2 ± 19.2 | 26.8 ± 14.9 | 42.0 ± 9.5 |
| Day 4 | 38.5 ± 18.1 | 22.8 ± 6.5 | 31.2 ± 10.9 |

As seen from the results in the above Table, transformation increases with a three or four day co-culture period after sonication.

Example 7

Immature soybean "Jack" cotyledons were treated as in Example 1 except that they were sonicated for 2 seconds in the presence of 1 ml Agrobacterium $OD_{600\ nm}$ 0.1 and then assayed at various time points after transfer to media containing cefotaxime as shown in Table VII. The results are presented below in Table VII.

TABLE VII

PERCENT TRANSFORMATION OF SOYBEAN COTYLEDONS DETERMINED AT INCREASING TIME IN CULTURE

| Days in Cefotaxime | Percent Surface Area Transformed (±SD) |
|---|---|
| Day 2 | 24.1 ± 11.2 |
| Day 7 | 17.2 ± 10.4 |

TABLE VII-continued

PERCENT TRANSFORMATION OF SOYBEAN COTYLEDONS
DETERMINED AT INCREASING TIME IN CULTURE

| Days in Cefotaxime | Percent Surface Area Transformed (±SD) |
|---|---|
| Day 14 | 10.3 ± 2.6 |
| Day 21 | 10.6 ± 3.2 |
| Day 28 | 3.8 ± 2.9 |

As can be seen in the above Table, the majority the β-glucuronidase expression decreases with time in culture which is believed to be due to two to factors. First, many of the cells that expressed GUS at day 2 were transiently transformed; the foreign DNA in the cytoplasm is degraded so that the transient cells stop expressing GUS. Also, with immature cotyledons only a few cells will divide and develop into somatic embryos while the other cells, regardless whether transformed or not, do not develop into embryos and senesce.

Example 8

The effect of acetosyringone was examined by preparing soybean "Chapman" cotyledons as in Example 1, except sonicating for 0, 1, 2 and 5 seconds and co-culturing with and without acetosyringone. Between eight and thirteen immature cotyledons were tested for each treatment. The results are presented in Table VIII.

TABLE VIII

PERCENT TRANSFORMATION OF SOYBEAN COTYLEDONS
CO-CULTURED WITH OR WITHOUT ACETOSYRINGONE

| | Percent Surface Area Transformed (±SD) | |
|---|---|---|
| Sonication Duration (seconds) | Media Lacking Acetosyringone | Media Containing Acetosyringone |
| 0 | 0.05 ± 0.16 | 0.44 ± 0.72 |
| 2 | 18.6 ± 14.4 | 44 ± 21.3 |
| 5 | 20.8 ± 15 | 45.7 ± 19.7 |

The presence of acetosyringone in the culture media approximately doubled the percent transformation of the sonication treatment. Similar results were shown with soybean "Jack". Acetosyringone is not critical for transformation, but it is preferred.

Example 9

Immature Soybean Cotyledons

Immature cotyledons from the cultivar "Jack" were divided into 8 groups; the first group was incised, and sonicated in the presence of Agrobacterium while the second group sonicated in the presence of Agrobacterium, but not incised. For comparison the third group was incised and sonicated but not inoculated with Agrobacterium, the fourth group was incised but not sonicated nor inoculated with Agrobacterium, the fifth group was incised, inoculated with Agrobacterium, but not sonicated, the sixth group was not incised, not sonicated but inoculated with Agrobacterium, the seventh group was not incised, not inoculated with Agrobacterium, but sonicated and the eighth group was not incised, not sonicated and not inoculated with Agrobacterium.

The cotyledons that were sonicated in the presence with Agrobacterium were treated as in Example 1 except that the cotyledons were sonicated for 2 seconds. The Agrobacterium EHA105 harboring Vec035 suspension was diluted to $O.D._{600\ nm}$ 0.1 from an overnight liquid culture described in Example 1. For the comparative examples the incisions were made by hand using a scalpel; three longitudinal incisions were made 1 mm apart at a depth of about 0.5 mm or about 50% of the cotyledon thickness. The cotyledons were co-cultured on D-40 medium containing 100 µM acetosyringone for two days and then transferred to D-40 medium containing 500 mg/L cefotaxime. Four days after treatment the cotyledons were assayed for GUS expression. The results are shown in Table IX.

TABLE IX

COMPARISON OF CONVENTIONAL METHOD
OF TRANSFORMATION TO SONICATION
METHOD OF TRANSFORMATION

| Techniques | | | % Surface Area |
|---|---|---|---|
| Incision | Sonication | Agrobacterium Inoculation | Transformed (± SD) |
| + | + | + | 16.3 ± 3.7 |
| − | + | + | 9.1 ± 3.4 |
| Comparative Ex & Controls | | | |
| + | + | − | 0 |
| + | − | − | 0 |
| + | − | + | 0 |
| − | − | + | 0 |
| − | + | − | 0 |
| − | − | − | 0 |

+ = with treatment
− = without treatment

As shown in the above Table, sonication and Agrobacterium are necessary to transform soybean cotyledons. The conventional method of incising the tissue is not effective, nor is simply exposing the cotyledon to the Agrobacterium.

Example 10

Soybean Shoot apices

Soybean "Chapman" seeds were germinated in aseptic conditions in culture tubes on ½ OMS media. At five days the seedlings were removed from the media and the young leaves surrounding the meristem were removed from the seedling. The plants were then inverted and placed in 15×200 mm borosilcate culture tubes containing an Agrobacterium EHA 105 containing Vec035 suspension the Agrobacterium concentration was 0.1 to 0.5 $OD_{600\ nm}$ of an overnight culture diluted in ½ OMS. The shoot apices were sonicated for 0, 30, 60, 120 or 300 seconds using the bath sonicator. After sonication, the shoot apices were placed on ½ OMS media, then 200 µl of the Agrobacterium suspension was dropped on each meristem and co-cultured for five days before assaying for GUS expression. Transformation was measured as the number of foci exhibiting blue, that is β-glucuronidase activity. The results are presented below in Table X.

15

TABLE X

| TRANSFORMATION OF SOYBEAN SHOOT APICES | | |
|---|---|---|
| Sonication Duration (Seconds) | Number of Apices | Number of GUS Positive Foci |
| 0 | 5 | 0 |
| 30 | 5 | 8 |
| 60 | 5 | 21 |
| 120 | 5 | 63 |
| 300 | 3 | 24 |

Again the sonication Agrobacterium treatment enhanced transformation of shoot apices.

Example 11

Soybean Somatic Embryos

Ten clumps of Soybean Chapman embryogenic suspension culture tissue, 2 to 4 mm in diameter in FN liquid medium, were transferred to sterile 13×100 mm borosilicate glass tubes. One ml of an overnight suspension of Agrobacterium EHA 105 containing Vec035, diluted to $OD_{600\ nm}$ 0.25 in FN medium, was added to the tissue. The suspension culture was sonicated for 0, 2, 5, 10, 20, 30 or 60 seconds. The suspension culture was then removed, blotted on filter paper and transferred to 30 ml FN medium in a baffled 125 ml DeLong flask. Acetosyringone was added to each flask at a concentration of 100 µM. The flasks were shaken at 150 rpm under 16 hours light at 25° C. After 2 days, portions of the suspension culture were assayed for GUS expression. The medium was replaced in the flasks with fresh FN medium containing 400 mg/L Timentin®. The flasks were incubated for an additional two days. β-glucuronidase expression was measured in the second set of suspension culture at four days after sonication treatment. Transformation events were scored as the total number of blue spots. The results are shown below in Table XI.

TABLE XI

| EFFECT OF SONICATION DURATION AND TIME IN CULTURE BEFORE ASSAYING FOR B-GLUCURONIDASE ACTIVITY ON SOYBEAN EMBRYOGENIC SUSPENSION CULTURES | | |
|---|---|---|
| Sonication Duration (seconds) | Number of Transformation Events 2 Days after Sonication | Number of Transformation Events 4 Days after Sonication |
| 0 | 7 | 0 |
| 2 | 479 | 803 |
| 5 | 643 | 637 |
| 10 | 797 | 643 |
| 20 | 441 | ND* |
| 30 | 364 | 1060 |
| 60 | 550 | 1807 |

ND* -- Data not available

Sonication increased the transformation in soybean embryogenic suspension cultures. The 60 second treatment gave the highest levels of expression, yet did not reduce the viability of the cells.

Example 12

Soybean embryogenic suspensions of the cultivar "Chapman" were treated as in Example 11 except the tissue was sonicated for 60 seconds. The tissue was co-cultivated in FN media containing 100 µM acetosyringone for one to four days. The media was removed and replenished daily. After the co-cultivation period, the medium was replaced with FN media containing 400 mg/l Timentin® antibiotic. GUS expression was assayed two days after the tissue was transferred to media containing Timentin® antibiotic. The results are shown in Table XII.

TABLE XII

| Days of co-cultivation | Number of Transformation Events |
|---|---|
| 1 | 8 |
| 2 | 2020 |
| 3 | 1498 |
| 4 | 1940 |

*Average of three repetitions

The data in the above table, indicate that increasing the duration of co-cultivation of the plant tissue with the Agrobacterium beyond one day, increases GUS expression in soybean embryonic suspensions.

Example 13

Soybean Somatic Embryos

Soybean "Chapman" embryogenic suspensions were treated as in Example 11 except that after sonication, the suspensions were co-cultured for two days in FN media containing 100 µM acetosyringone. After co-culture, the suspensions were placed in FN media containing 400 mg/l Timentin®. Ten days after sonication, the suspensions were placed in FN media containing 400 mg/l Timentin® and 20 mg/l hygromycin; thereafter the medium was replenished weekly.

Six to nine weeks after sonication, eight stably transformed clones were isolated from the sonicated suspensions and separately subcultured. Growth of the soybean tissue in the presence of hygromycin-containing medium establishes the presence and expression of the hygromycin resistance gene. GUS assays performed on these clones confirmed the expression of the introduced β-glucuronidase gene. Control treatments which received Agrobacterium without sonication, did not produce any clones.

Example 14

Soybean Somatic Embryos

Soybean embryogenic suspensions of the cultivar "Jack" were treated as in Example 11 except after the sonication step, the tissue was co-cultivated for one day in FN media containing 100 µM acetosyringone.

One hygromycin-resistant, GUS-expressing clone was obtained from a 30 second sonication treatment. It is believed that this soybean cell line has not been transformed by any other method for transforming plant tissue. The sonication method of the present invention transforms recalcitrant tissue.

Example 15

Buckeye Embryogenic Suspensions

Ten clumps of buckeye embryogenic cells, about 5 mm in diameter, were placed in a 1.5 ml Eppendorf microcentrifuge tube containing 1.0 ml of an overnight suspension of Agrobacterium EHA 105. The Agrobacterium which contains Vec035 was diluted to $OD_{600\ nm}$ 0.5 in FN media. Buckeye cells were sonicated as in Example 11 except the duration of the sonication was either 0, 1, 2, 5, 10 or 20 seconds. After sonication, the clumps were blotted on filter paper and then placed in 125 ml flasks containing 30 ml of FN media, containing 100 μM acetosyringone and shaken on an orbital shaker at 150 rpm for two days. The cultures were then placed in fresh FN media containing 400 mg/L Timentin®. The β-glucuronidase expression was assayed six days after sonication. Transformation efficiency was measured as the number of blue foci. The results are shown below in Table XV.

TABLE XV

PERCENT TRANSFORMATION OF
BUCKEYE EMBRYOGENIC SUSPENSION CELLS

| Sonication Duration (seconds) | Number of GUS Positive Foci |
|---|---|
| 0 | 0 |
| 1 | 0 |
| 2 | 25 |
| 5 | 1 |
| 10 | 0 |
| 20 | 112 |

The sonication treatment increases the number of transformation events in buckeye tissue. Again, transformation efficiency increases with increasing length of sonication treatment.

Example 15a

Buckeye Embryogenic Suspensions

Ten clumps of buckeye embryogenic cells, about 5 mm in diameter, were treated as in Example 15 except the duration of the sonication was either 0, 7.5, 15, 30 or 60 seconds and the cells were incubated for three days in FN media containing 100 μM acetosyringone. The cultures were then placed in a fresh FN media containing 400 mg/L Timentin® and 20 mg/L hygromycin to select for transformed cells. The media was replenished every two weeks. Ten weeks after sonication clones were isolated and β-glucuronidase expression was assayed. Sonication transformation of the buckeye embryonic suspension produced hundreds of GUS-positive, hygromycin resistant, stably-transformed clones.

Example 16

Cowpea Leaflets

Cowpea leaflets were sterilized in 20% Clorox® bleach, 0.02% Tween 20 for 20 minutes, rinsed three times with distilled water and cut into 1 to 2 cm square pieces. Leaf pieces were placed in a 50 ml polypropylene conical tube containing an Agrobacterium EHA 105 containing Vec035, suspension $OD_{600\ nm}$ 0.5 of an overnight culture diluted in on OMS medium containing 1 mg/L benzyladenine and 1 mg/L NAA. The cells were sonicated for 0, 2, 10 or 60 seconds in a Fisherbrand FS5 bath sonicator. Leaf pieces were then removed, blotted with filter paper and placed on a CM media containing 100 μM acetosyringone for two days. The cowpea leaf pieces were then placed in CM medium containing 500 mg/L cefotaxime for two days and then assayed for β-glucuronidase expression. Transformation efficiency was measured as the percent of surface area exhibiting blue sectors. The results, which are the accumulation of two independent experiments, are shown in Table XVI.

TABLE XVI

PERCENT TRANSFORMATION OF COWPEA LEAFLETS

| Sonication Duration (seconds) | Percent Transformation |
|---|---|
| 0 | 0.5% |
| 2 | 15% |
| 10 | 27% |
| 60 | 42% |

As seen in the above table, the sonication treatment increases the percent transformation in cowpea leaves when compared to the controls. Moreover, the percent transformation increases as the length of the sonication treatment increases.

Example 17

Tobacco Seedlings

Four day old tobacco seedlings aseptically grown on one half strength OMS media containing 3% sucrose and 0.2% Gelrite were sonicated in 50 ml polypropylene tubes containing an Agrobacterium EHA105 containing Vec035 suspension. The Agrobacterium which had $OD_{600\ nm}$ 0.1 to 0.5 was an overnight culture diluted in one half strength OMS medium. The seedlings were sonicated for 0, 5, 10, 30, 60, 120 or 300 seconds using the bath sonicator. After sonication the seeds and seedlings were blot-dried on filter paper, placed on one half strength OMS medium containing 100 μM acetosyringone, and 0.2% Gelrite, at pH 5.7 and co-cultivated for two days. Seedlings were then placed on one half strength OMS medium containing 400 mg/L Timentin® and 0.2% Gelrite, at pH 5.7 for two days. β-glucuronidase expression was assayed after this treatment.

TABLE XVII

EFFECT OF VARYING SONICATION DURATION
ON TRANSFORMATION OF TOBACCO SEEDLINGS

| Sonication Duration (seconds) | Number of Seedlings | Number of Transformation Events | Average Number of Transformation Events/Seedling |
|---|---|---|---|
| 0 | 21 | 37 | 1.76 |
| 5 | 35 | 79 | 2.26 |
| 10 | 21 | 127 | 6.04 |
| 30 | 31 | 125 | 4.03 |
| 60 | 30 | 164 | 5.47 |
| 120 | 22 | 48 | 2.18 |
| 300 | 24 | 137 | 5.7 |

The sonication treatment increases the percent transformation of tobacco seedlings. The expression of the β-glucuronidase gene introduced in the tobacco seedlings was observed in the tissue which developed from the seedling: roots, stems, leaves, petioles and shoot apices containing meristems.

Example 18

Tobacco seedlings were prepared and treated as in Example 17; except that the sonication duration was 0, 1, 5 and 10 seconds and the sonication wattage was varied as shown in Table XVIII. In addition, 10 seedlings were used in each group. Also the sonication was preformed using a probe sonicator using a Branson Sonifier Model #350 having a tapered microtip with an output between 10 and 45 watts.

TABLE XVIII

EFFECT OF VARYING SONICATION DURATION ON TRANSFORMATION OF TOBACCO SEEDLINGS

| Sonication Duration (seconds) | Sonicator Output Setting (watts) | Number of Transformation Events |
|---|---|---|
| 0 | 0 | 126 |
| 1 | 10 | 243 |
| 5 | 10 | 121 |
| 10 | 10 | 115 |
| 1 | 27 | 713 |
| 5 | 27 | 963 |
| 10 | 27 | 910 |
| 5 | 45 | 849 |
| 10 | 45 | 574 |

Probe-type sonicators can also be effectively used in addition to bath sonicators.

Example 19

Maize Embryos

Maize plants A6232 were grown either under standard greenhouse conditions or in the field. Immature embryos 3 mm in length obtained 15 days after pollination, were isolated and placed on 2T2S medium which contains 0.2% Gelrite at pH 5.7. The embryos were transferred to 1.5 ml microcentrifuge tubes containing a 1 ml suspension of an overnight Agrobacterium strain EHA 105 which harbors pIG121Hm, diluted to $OD_{600\ nm}$ 0.25 with 2T2S liquid medium at pH 5.7. The plasmid pIG121Hm contain a 35S promoter with a castor bean intron and the coding region for GUS. The embryos were then sonicated for either 0, 0.5, 1, 3, 10, 30, 100, 300 or 600 seconds. After sonication the maize embryos were blotted on filter paper and placed scutellum side up on 2T2S media which also contained 100 µM acetosyringone and 0.2% Gelrite, at pH 5.7. Three to four days after sonication, the embryos were transferred to 2T2S media which contained 500 mg/L cefotaxime and 0.2% Gelrite at pH 5.7. Embryos were assayed for transient GUS expression seven days after sonication. Transformation was measured as the percentage of the surface area of the scutellum that was blue, that is GUS positive. The results are presented in Table XIX.

TABLE XIX

PERCENT TRANSFORMATION OF MAIZE IMMATURE EMBRYOS

| Sonication Duration (sec) | % Surface Area Transformed (± SD) |
|---|---|
| 0 | 0.06 ± 0.06 |
| 0.5 | 15.6 ± 12.5 |
| 1 | 9 ± 6.4 |
| 3 | 59.5 ± 20.6 |
| 10 | 61.5 ± 15.9 |
| 30 | 80.3 ± 8.3 |
| 100 | 82.4 ± 9.7 |
| 300 | 83.7 ± 7.4 |
| 600 | 68.5 ± 7.3 |

The GUS expression rates were increased 150–1400 fold over the controls by sonicating the maize embryos in the presence of the Agrobacterium.

Example 20

Conifer Seedlings

White spruce seedlings were germinated in the dark at 23° C. on half strength OMS media. Fourteen days after plating, the germinated seedlings were placed in 13×100 mm borosilicate glass test tubes with 2 ml of an overnight suspension of either Agrobacterium EHA 105 harboring Vec035 or EHA 105 harboring pIG121Hm. The Agrobacterium was diluted to an $O.D._{600\ nm}$ 0.5 in liquid CN medium. The seedlings were sonicated for 0, 5, or 50 seconds. After sonication, the seedlings were incubated in the Agrobacterium suspension for a total of five minutes and then blot-dried on sterile filter paper. Seedlings were co-cultured in the dark at 23° C. on CN media with 100 µM acetosyringone for three days then transferred to CN media with 500 mg/L cefotaxime. Seven days after sonication, the seedlings were assayed for GUS expression. Percent surface area transformed was measured as the average number of blue spots per seedling. The results are presented in Table XX.

TABLE XX

GUS-POSITIVE FOCI IN CONIFER SEEDLINGS

| Sonication Duration (seconds) | Number of GUS-positive Foci using EHA 105 Vec035 | Number of GUS-positive Foci using EHA 105 pIG121Hm |
|---|---|---|
| 0 | 0 | 0 |
| 5 | 4 | 32 |
| 50 | 26 | 5 |

As shown in the above Table, the sonication increases transformation in conifers.

Example 21

Wheat seeds of the variety "Bobwhite" were surface sterilized as in Example 1 and plated on half strength OMS media. After germinating the seeds at 23° C. for five days the seedlings were transferred to 150 mm×23 mm borosilicate tubes and 10 to 15 ml of Agrobacterium suspension was added to the tubes. The Agrobacterium suspension was from an overnight culture of EHA105 pIG121Hm washed and diluted to an $O.D._{600\ nm}$ 0.2 with half strength liquid OMS media. The seedlings were sonicated for 0, 2, 10, 30 and 100 seconds then co-cultured on half strength OMS media at 23° C. for three days and then transferred to half strength OMS media containing 400 mg/L Timentin®. The tissue was assayed for GUS expression five days after sonication. Results are shown below in Table XXI.

TABLE XXI

EFFECT OF VARIOUS SONICATION DURATIONS ON TRANSFORMATION OF WHEAT SEEDLINGS

| Sonication duration (sec) | Number of GUS positive foci |
|---|---|
| 0 | 0 |
| 2 | 3 |
| 10 | 10 |
| 30 | 1 |
| 100 | 28 |

In the 2, 10, and 30 second sonication treatments, all transformed cells were located in the root. Most of the transformations were localized at the root tip, at or near the meristematic tissue. The 100 second treatment had 4 transformation events that were in the leaf tissue and 7 that were in the scutellum. Each of these eleven events were observed as rows of GUS positive cells (4 to 8 cells), which indicates that a single stably-transformed cell in each row divided several times to produce the row of GUS positive, transformed cells.

Transformation has also been obtained in clover.

The invention is not limited to the embodiments which have just been described. The invention is intended by the following claims to include all technically equivalent means which come within the full scope and true spirit of the invention.

What is claimed is:

1. A method for transforming a plant sample comprising the following steps:
   a. providing a non-tumor inducing vector containing nucleic acid to be transferred to the plant sample, wherein the vector is a non-tumor inducing Agrobacterium;
   b. combining the plant sample with said vector;
   c. sonicating the plant sample; wherein the vector is combined with the plant sample before, during, or after sonication;
   d. lastly growing the plant sample and selecting for the transformed plant sample.

2. The method of claim 1, further comprising the step of confirming that the transformation is stable after step d.

3. The method of claim 2, wherein the plant sample is sonicated in the presence of the vector.

4. The method of claim wherein the Agrobacterium is *Agrobacterium tumefaciens*.

5. The method of claim 1, further comprising the step of:
   e. culturing the plant sample in the presence of the vector for at least 1 day after sonication.

6. The method of claim 1, wherein the sonication duration is from 0.1 seconds to 15 minutes.

7. The method of claim 1, wherein the plant sample is sonicated for at least about 0.1 seconds.

8. The method of claim 1, wherein the plant sample is sonicated for less than 60 seconds.

9. The method of claim 1, wherein the plant sample is sonicated for less than 6 minutes.

10. The method of claim 1, further comprising the step of:
    culturing the plant sample, after steps (b) and (c), in the presence of an antibiotic to inhibit the growth of the vector.

11. The method of claim 5, further comprising the step of:
    culturing the plant sample, after step (e) in the presence of a antibiotic to inhibit the growth of the vector.

12. The method of claim 1 wherein the vector is Agrobacterium, the plant sample is sonicated in the presence of the vector, from about 0.1 seconds to about 5 minutes.

13. The method of claim 1, wherein acetosyringone is present in the culture medium in an effective amount to stimulate transformation.

14. The method of claim 1, wherein acetosyringone is present in the culture medium from about 1 µM to about 1 mM.

15. The method of claim 1, wherein acetosyringone is present in the culture medium from about 100 µM to about 200 µM.

16. The method of claim 1, wherein the plant sample is an embryogenic suspension and the sonication duration is less than six minutes.

17. The method of claim 1 wherein the nucleic acid is DNA.

18. The method of claim 1, wherein the vector further comprises a reporter gene and wherein a plant sample which expresses the gene is selected.

19. The method of claim 1 wherein the vector further comprises a selectable marker gene and the plant sample is grown on a medium which selects for plant samples that contain the selectable marker gene.

* * * * *